United States Patent
Oshinski et al.

(10) Patent No.: US 11,311,459 B2
(45) Date of Patent: Apr. 26, 2022

(54) SYRINGE ADAPTER WITH ASPIRATION ASSEMBLY

(71) Applicant: Becton Dickinson and Company Limited, Dun Laoghaire (IE)

(72) Inventors: Matthew Oshinski, Andover, NJ (US); Antonio Righez Mesquita, Wayne, NJ (US)

(73) Assignee: Becton Dickinson and Company Limited, Dun Laoghaire (IE)

( * ) Notice: Subject to any disclaimer, the term of this patent is extended or adjusted under 35 U.S.C. 154(b) by 316 days.

(21) Appl. No.: 16/381,464

(22) Filed: Apr. 11, 2019

(65) Prior Publication Data

US 2019/0321261 A1   Oct. 24, 2019

Related U.S. Application Data

(60) Provisional application No. 62/659,840, filed on Apr. 19, 2018.

(51) Int. Cl.
*A61J 1/20*   (2006.01)

(52) U.S. Cl.
CPC ............ *A61J 1/2096* (2013.01); *A61J 1/201* (2015.05); *A61J 1/2037* (2015.05); *A61J 1/2048* (2015.05); *A61J 1/2082* (2015.05)

(58) Field of Classification Search
CPC ........ A61J 1/2096; A61J 1/201; A61J 1/2037; A61J 1/2048; A61J 1/2082
See application file for complete search history.

(56) References Cited

U.S. PATENT DOCUMENTS

| | | | |
|---|---|---|---|
| 4,576,211 A * | 3/1986 | Valentini | A61J 1/2096 141/329 |
| 7,134,641 B2 | 11/2006 | Jensen et al. | |
| 8,454,579 B2 | 6/2013 | Fangrow, Jr. | |
| 10,022,301 B2 | 7/2018 | Ivosevic et al. | |
| 10,052,259 B2 | 8/2018 | Ivosevic et al. | |
| 10,561,802 B2 | 2/2020 | Kim et al. | |
| 2013/0076019 A1 | 3/2013 | Takemoto | |

(Continued)

FOREIGN PATENT DOCUMENTS

| | | |
|---|---|---|
| CN | 101288786 A | 10/2008 |
| CN | 102448537 A | 5/2012 |

(Continued)

*Primary Examiner* — Timothy P. Kelly
(74) *Attorney, Agent, or Firm* — The Webb Law Firm

(57) ABSTRACT

A syringe adapter includes a housing having a first end and a second end positioned opposite the first end, with the housing including a connector body positioned at the first end of the housing and configured to be secured to a syringe barrel, a cannula positioned within the housing, with the cannula defining a transfer opening and a valve opening, a seal arrangement positioned within the housing and movable within the housing, and an aspiration assembly comprising an aspiration housing defining an aspiration opening, a filter received by the aspiration housing, and one-way valve received by the aspiration housing, where the valve opening of the cannula is positioned within the aspiration housing, and where air is configured to flow into the filter via the aspiration opening, into the one-way valve, and into the valve opening of the cannula.

20 Claims, 15 Drawing Sheets

(56) References Cited

U.S. PATENT DOCUMENTS

| | | | |
|---|---|---|---|
| 2013/0079744 A1* | 3/2013 | Okiyama | A61J 1/2096 604/408 |
| 2014/0261877 A1* | 9/2014 | Ivosevic | A61J 1/201 141/27 |
| 2015/0297454 A1 | 10/2015 | Sanders et al. | |
| 2018/0028402 A1 | 2/2018 | Krheli et al. | |
| 2018/0147359 A1 | 5/2018 | Seok et al. | |

FOREIGN PATENT DOCUMENTS

| | | |
|---|---|---|
| CN | 106237421 A | 12/2016 |
| CN | 107635600 A | 1/2018 |
| EP | 2589367 A1 | 5/2013 |
| EP | 2606872 B1 | 7/2014 |
| JP | 2016511121 A | 4/2016 |
| JP | 2018034037 A | 3/2018 |
| WO | 2015134777 A1 | 9/2015 |

\* cited by examiner

SYRINGE ADAPTER WITH ASPIRATION ASSEMBLY

CROSS-REFERENCE TO RELATED APPLICATION

The present application claims priority to U.S. Provisional Application Ser. No. 62/659,840, entitled "Syringe Adapter with Aspiration Assembly", filed Apr. 19, 2018, the entire disclosure of which is hereby incorporated by reference in its entirety.

BACKGROUND OF THE INVENTION

Field of the Invention

The present invention relates to a syringe adapter for connecting a syringe to another medical device or fluid container and, more particularly, to a syringe adapter including an aspiration assembly.

Description of Related Art

Healthcare clinicians, such as pharmacists and nurses, can be subject to acute and long term health risks as a result of repeated exposure to drugs or solvents, which may escape into the air during drug preparation, drug administration, and other similar handling activities. For example, when performing infusions, it is often necessary to inject a drug or other medical substance into an infusion fluid inside an infusion bag or other infusion fluid container. This injection is often performed by penetrating a septum or other fluid barrier of an injection port on the infusion bag or on the infusion fluid line with a needle of a syringe filled with the medical fluid in question. Before penetrating the septum, it may also be necessary to transfer the medical fluid from a vial to a syringe and then from the syringe to the container. In each of these steps, the clinician or care provider may be exposed to the medical fluid resulting in contamination from, for example, vaporized medical fluids or from contaminants released as an aerosol. For example, contamination may occur by breathing the vaporized or aerosol contaminates into the lungs. Contamination may also occur when vaporized or aerosol contaminants condense on and then penetrate the clinician's or care provider's skin. In some instances, such condensed contaminates may even penetrate protective gloves.

Unfortunately, exposure to contaminants may, on a long term basis, give rise to unacceptably high concentrations of medicament or contaminants in the clinician's or care provider's blood or body tissue. Risk of contamination is increased due to the many transferring steps between containers which must occur during preparation of complex infusions. For these reasons, closed system transfer devices (CSTDs) have been developed to ensure that the medicament is contained in the transfer device during transfer of the medicament. A CSTD generally includes a syringe adapter for connection to a syringe and another adapter for connection to a vial, a second syringe, a fluid container, or a conduit providing fluid access to the patient's circulatory system. In use, the clinician or care provider may reconstitute a powdered or lyophilized compound with saline or some other reconstitution medium by attaching the syringe to the vial via connection of the respective adapters. The drug is then reconstituted by injecting fluid from the syringe, through the respective adapters, and into the vial. In some instances, the reconstituted infusion may then be aspirated into the syringe. After aspiration, the adapters can be disconnected from one another. The clinician or care provider may then attach the syringe to another adapter to transfer fluid from the syringe to a fluid conduit or patient delivery device, such as an IV line or syringe, for administration to the patient. In certain circumstances, air is first aspirated into a syringe and injected into a vial prior to withdrawal of fluid from the vial. Injecting the vial with air pressurizes the vial such that when fluid is withdrawn from the vial, the pressure within the vial returns to its original pressure.

SUMMARY OF THE INVENTION

According to one aspect of the disclosure, a syringe adapter includes a housing having a first end and a second end positioned opposite the first end, with the housing including a connector body positioned at the first end of the housing and configured to be secured to a syringe barrel, a cannula positioned within the housing, with the cannula having a first end and a second end opposite the first end and defining a transfer opening and a valve opening, a seal arrangement positioned within the housing and movable within the housing, with the seal arrangement including a membrane, and an aspiration assembly positioned within the housing. The aspiration housing includes an aspiration housing defining an aspiration opening, a filter received by the aspiration housing, and one-way valve received by the aspiration housing, where the valve opening of the cannula is positioned within the aspiration housing, and where air is configured to flow into the filter via the aspiration opening, into the one-way valve, and into the valve opening of the cannula.

The aspiration assembly may further include a base secured to the aspiration housing and engaging the filter and the one-way valve. The base may be secured to the connector body. The first end of the cannula may be secured to the connector body, with the cannula extending through the base, the one-way valve, the filter, and the aspiration housing with the second end of the cannula configured to be received by the seal arrangement. The one-way valve may prevent the flow of fluid from the one-way valve to the filter and to the aspiration opening of the aspiration housing. The seal arrangement may have a first position with the second end of the cannula received within the membrane of the seal arrangement and a second position with the second end of the cannula positioned outside of the membrane of the seal arrangement, with the membrane of the seal arrangement engaging and sealing the aspiration opening of the aspiration housing when the seal arrangement is in the second position. At least a portion of the aspiration assembly may be received within the connector body. The valve opening of the cannula may include a plurality of openings. The filter and the one-way valve may be annular, with the one-way valve received within the filter. The one-way valve may include a valve body and a valve member moveable radially inward relative to the valve body. The valve member of the one-way valve may be elastomeric.

In a further aspect, a syringe adapter includes a housing having a first end and a second end positioned opposite the first end, with the housing including a connector body positioned at the first end of the housing and configured to be secured to a syringe barrel, a cannula positioned within the housing, with the cannula having a first end and a second end opposite the first end, a seal arrangement positioned within the housing and movable within the housing, with the seal arrangement including a membrane, and an aspiration assembly positioned within the housing. The aspiration assembly includes an aspiration housing defining an aspiration opening, a filter received by the aspiration housing, and a one-way valve received by the aspiration housing, where air is configured to flow into the aspiration housing via the aspiration opening, through the one way valve, and through the filter.

The aspiration assembly may further include a base secured to the aspiration housing and engaging the filter. The base may define an opening and the connector body may define an opening in fluid communication with the opening of the base and a central passageway of the connector body. The connector body may define an opening in fluid communication with the aspiration housing and a central passageway of the connector body, where air is configured to pass through the filter and enter the opening of the connector body. The first end of the cannula may be secured to the connector body, with the cannula extending through the filter, the one-way valve, and the aspiration housing with the second end of the cannula configured to be received by the seal arrangement. The one-way valve may prevent the flow of fluid from within the aspiration housing to the aspiration opening. The seal arrangement may have a first position with the second end of the cannula received within the membrane of the seal arrangement and a second position with the second end of the cannula positioned outside of the membrane of the seal arrangement, with the seal arrangement engaging and sealing the aspiration opening of the aspiration housing when the seal arrangement is in the second position. One of the membrane and a sealing gasket may seal the aspiration opening of the aspiration housing when the seal arrangement is in the second position. The one-way valve may be an umbrella valve.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

DESCRIPTION OF THE INVENTION

Figure 1:
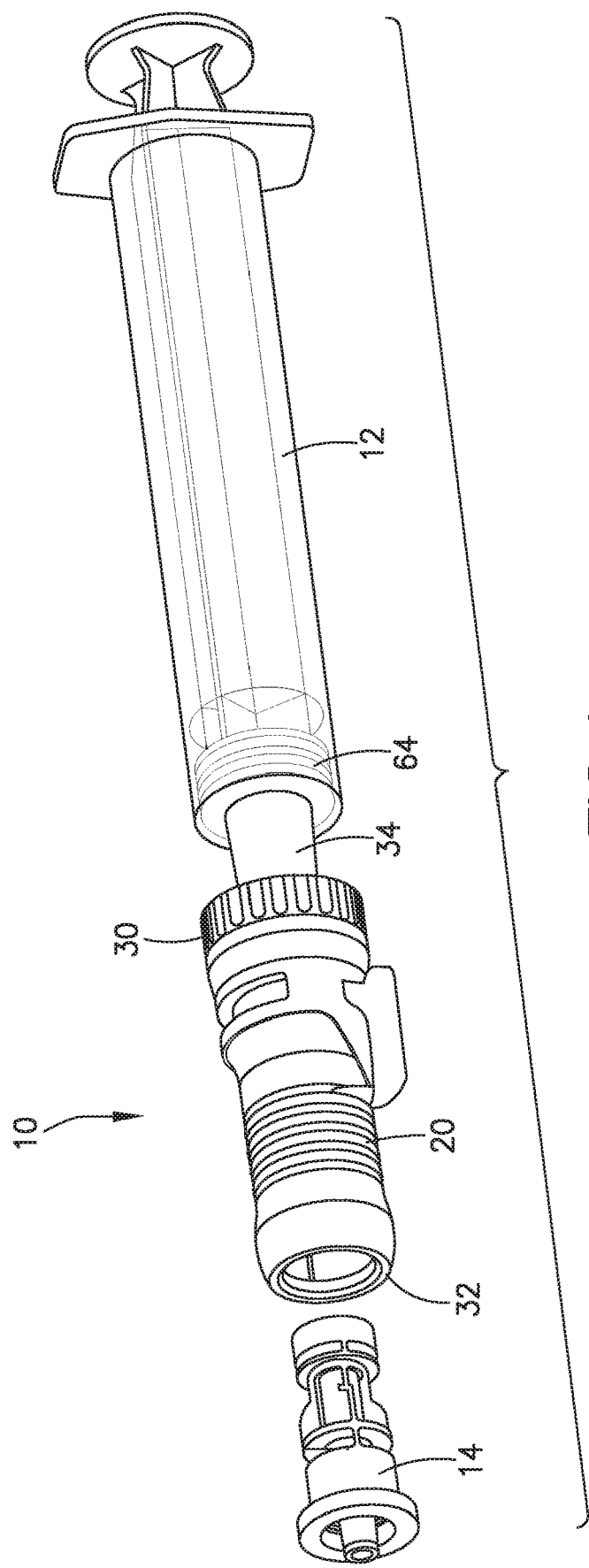
FIG. 1 is a perspective view of a syringe adapter according to one aspect of the present invention.
Figure 2:
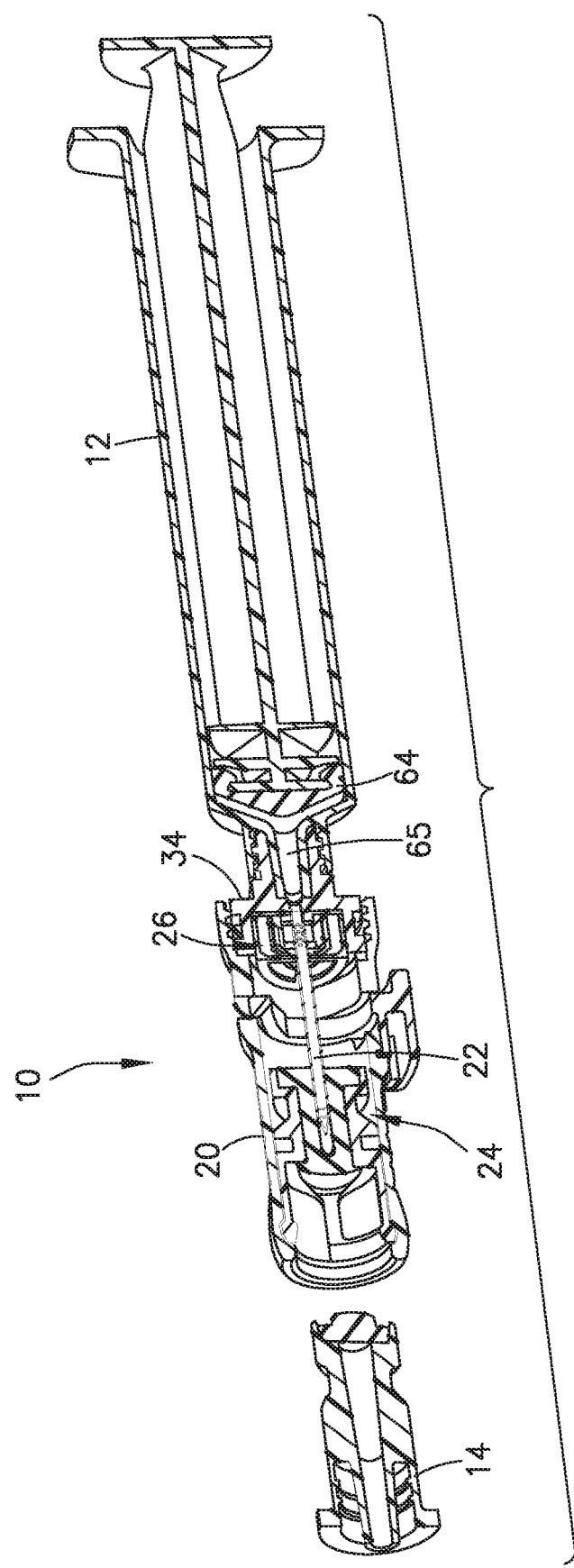
FIG. 2 is a cross-sectional view of the syringe adapter of FIG. 1.
Figure 3:
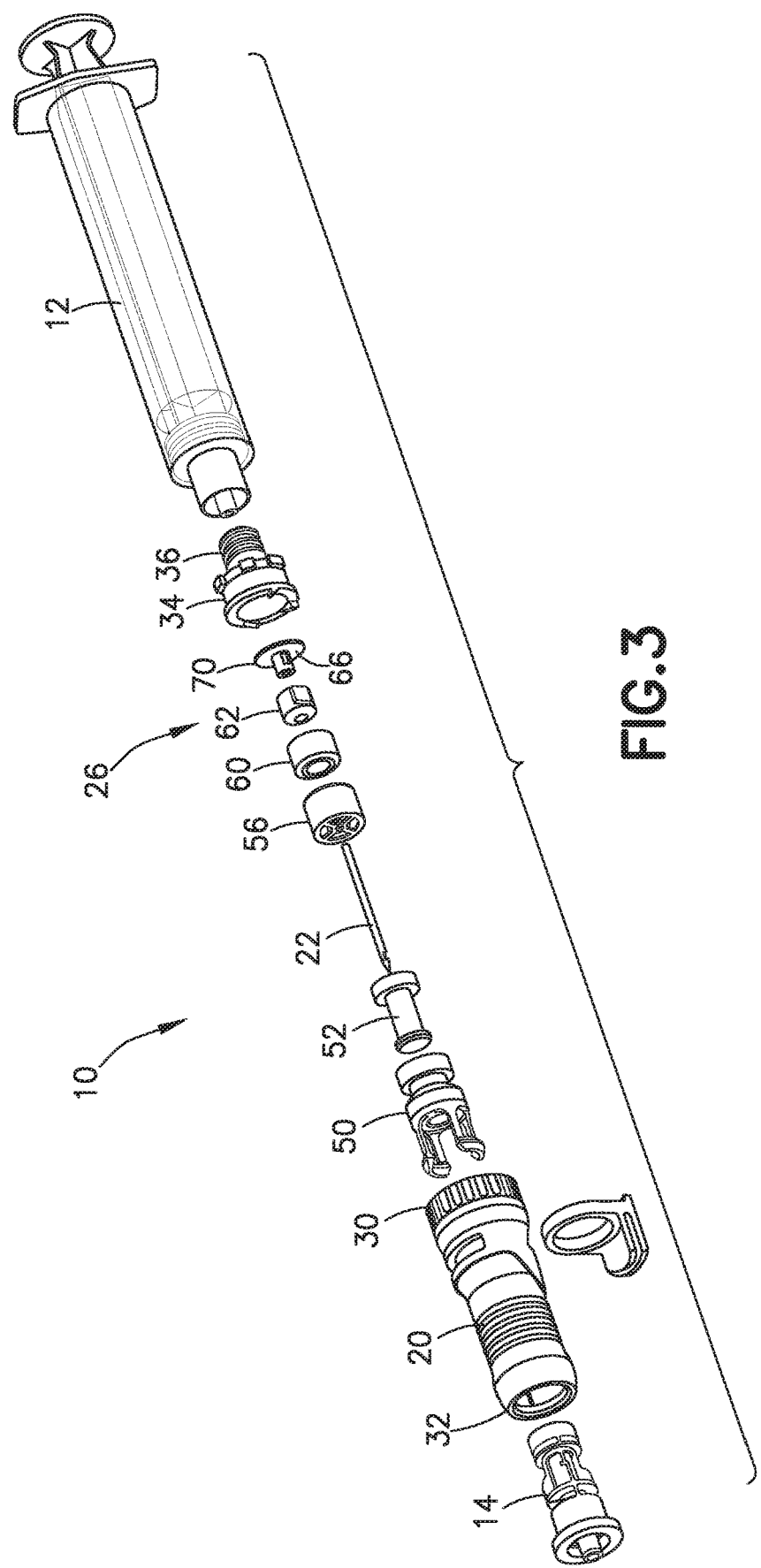
FIG. 3 is an exploded perspective view of the syringe adapter of FIG. 1.
Figure 4:
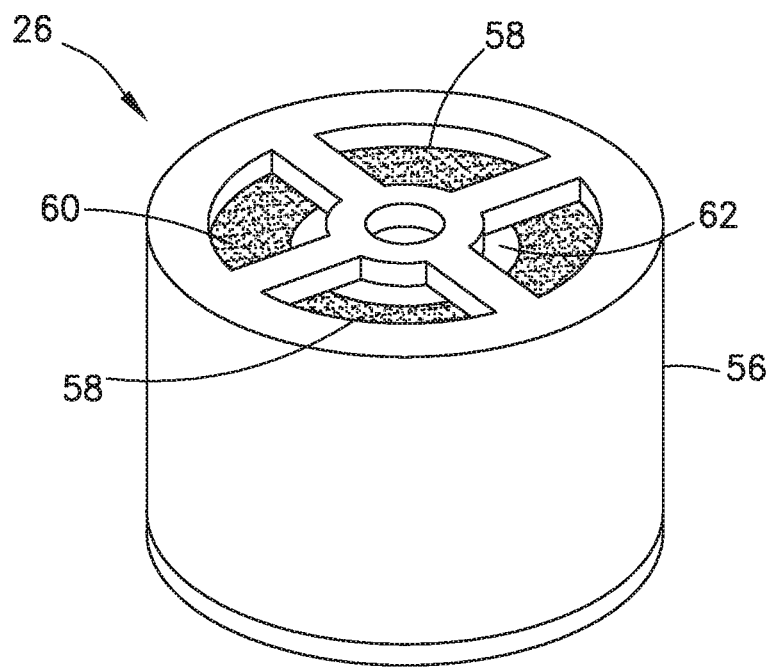
FIG. 4 is a perspective view of an aspiration assembly according to one aspect of the present invention.
Figure 5:
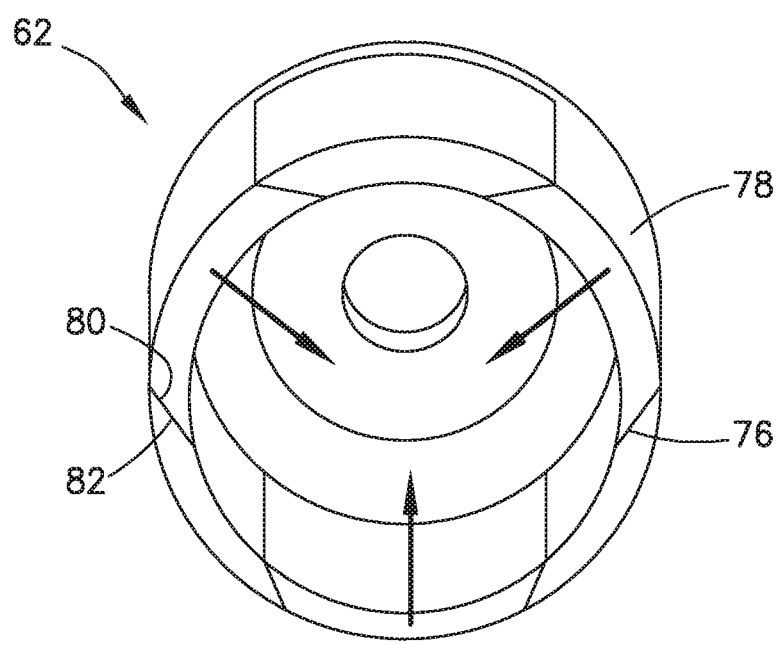
FIG. 5 is a perspective view of a one-way valve according to one aspect of the present invention.

The illustrations generally show preferred and non-limiting aspects of the systems and methods of the present disclosure. While the descriptions present various aspects of the devices, it should not be interpreted in any way as limiting the disclosure. Furthermore, modifications, concepts, and applications of the disclosure's aspects are to be interpreted by those skilled in the art as being encompassed by, but not limited to, the illustrations and descriptions herein.

Further, for purposes of the description hereinafter, the terms "end", "upper", "lower", "right", "left", "vertical", "horizontal", "top", "bottom", "lateral", "longitudinal", and derivatives thereof shall relate to the disclosure as it is oriented in the drawing figures. The term "proximal" refers to the direction toward the center or central region of the device. The term "distal" refers to the outward direction extending away from the central region of the device. However, it is to be understood that the disclosure may assume various alternative variations and step sequences, except where expressly specified to the contrary. It is also to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting. For the purpose of facilitating understanding of the disclosure, the accompanying drawings and description illustrate preferred aspects thereof, from which the disclosure, various aspects of its structures, construction and method of operation, and many advantages may be understood and appreciated.

According to an aspect of the disclosure, a syringe adapter 10 for connecting a syringe 12 to another medical device, such as a patient connector 14, or fluid container is provided.

The medical device can be, for example, a patient line, vial adapter, fluid container, or infusion adapter. In other examples, the container can be a medical vial, syringe barrel, IV bag, or similar container for holding a fluid to be administered to a patient. The syringe adapter 10 can be used to facilitate closed transfer of fluids between the syringe 12 and medical device or fluid container.

Referring to FIGS. 1-9, the syringe adapter 10 according to one aspect of the present invention includes a housing 20, a cannula 22 positioned within the housing 20, a seal arrangement 24 positioned within the housing 20 and movable within the housing 20 between first and second positions, and an aspiration assembly 26 positioned within the housing 20. The aspiration assembly 26 is configured allow the syringe 12 to aspirate air into the syringe 12 while the syringe adapter 10 is connected to the syringe 12. As noted above, in certain circumstances, aspirating air into the syringe 12 while connected to the syringe adapter 10 is desirable to allow air to be injected into a vial or other container. Without the aspiration arrangement, the seal arrangement 24 would prevent air from being aspirated into the syringe 12 when connected to the syringe adapter 10.

The housing 20 has a first end 30 and a second end 32 positioned opposite the first end 30 and includes a connector body 34 positioned at the first end 30 of the housing 20. The connector body 34 is configured to be secured to the syringe 12. In one aspect, the connector body 34 includes a female luer connector 36, although other suitable connection arrangements may be utilized. The cannula 22 has a first end 40 and a second end 42 opposite the first end 40. The cannula 22 defines a transfer opening 44 and a valve opening 46. The transfer opening 44 is positioned adjacent to the second end 42 of the cannula 22. The valve opening 46 is positioned intermediate the first and second ends 40, 42 of the cannula 22. The seal arrangement 24 includes a collet 50 and a membrane 52 received within the collet 50, although other suitable seal arrangements 24 may be utilized. The seal arrangement 24 has a first position with the second end 42 of the cannula 22 received within the membrane 52 of the seal arrangement 24 and a second position with the second end 42 of the cannula 22 positioned outside of the membrane 52 of the seal arrangement 24. The seal arrangement 24 facilitates the closed transfer of fluid utilizing the syringe adapter 10. The collet 50 cooperates with a mating connector, such as the patient connector 14, to connect the collet 50 to the mating connector and to transition the seal arrangement 24 from the first position to the second position to allow fluid to flow through the cannula 22. The seal arrangement 24 is not discussed in detail herein and may function similarly to the seal arrangement shown and described in United States Patent Appl. Pub. No. 2015/0297454, which is incorporated by reference herein in its entirety.

Figure 6:
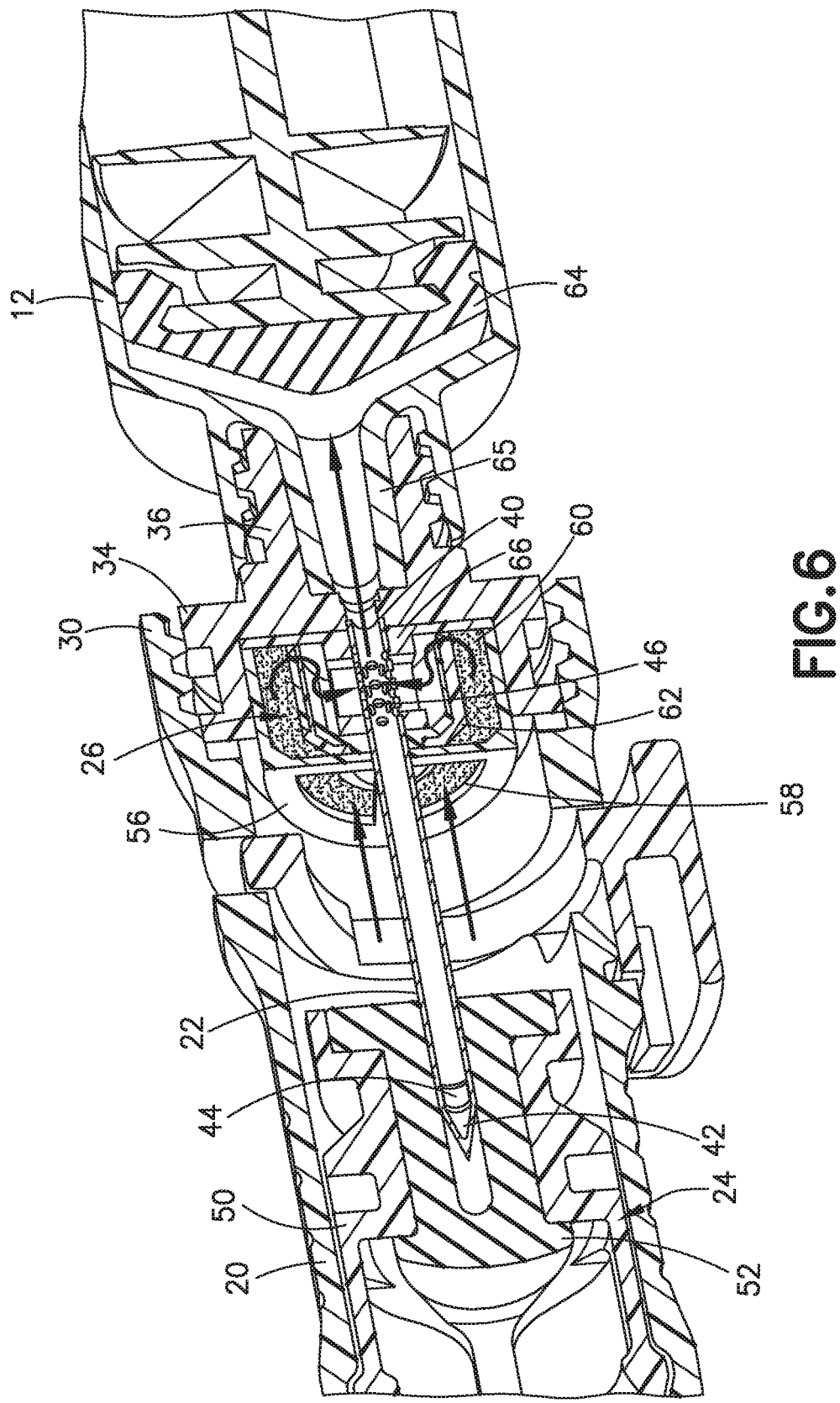
FIG. 6 is a partial cross-sectional view of the syringe adapter of FIG. 1, showing an aspiration flow path.

Referring to FIGS. 3-9, the aspiration assembly 26 includes an aspiration housing 56 defining an aspiration opening 58, a filter 60 received by the aspiration housing 56, and a one-way valve 62 received by the aspiration housing 56. As shown in FIG. 6, air is configured to flow into the filter 60 via the aspiration opening 58, into the one-way valve 62, and into the valve opening 46 of the cannula 22. More specifically, when a syringe plunger 64 is withdrawn, a pressure drop is created within the aspiration housing 56 to open the one-way valve 62 to aspirate air through the housing 20, through the aspiration opening 58, through the filter 60, through the one-way valve 62, into the cannula 22 via the valve opening 46, through a central passageway 65 of the connector body 34, and into the syringe 12.

The aspiration assembly 26 may also include a base 66 secured to the aspiration housing 56 and engaging the filter 60 and one-way valve 62. The base 66 may be secured to the connector body 34. The base 66 may be secured to the aspiration housing 56 and the connector body 34 via ultrasonic welding, although other suitable securing arrangements may also be utilized. The first end 40 of the cannula 22 is secured to the connector body 34 with the cannula 22 extending through the base 66, the one-way valve 62, the filter 60, and the aspiration housing 56, with the second end 42 of the cannula 22 configured to be received by the seal arrangement 24, as discussed above.

Figure 7:
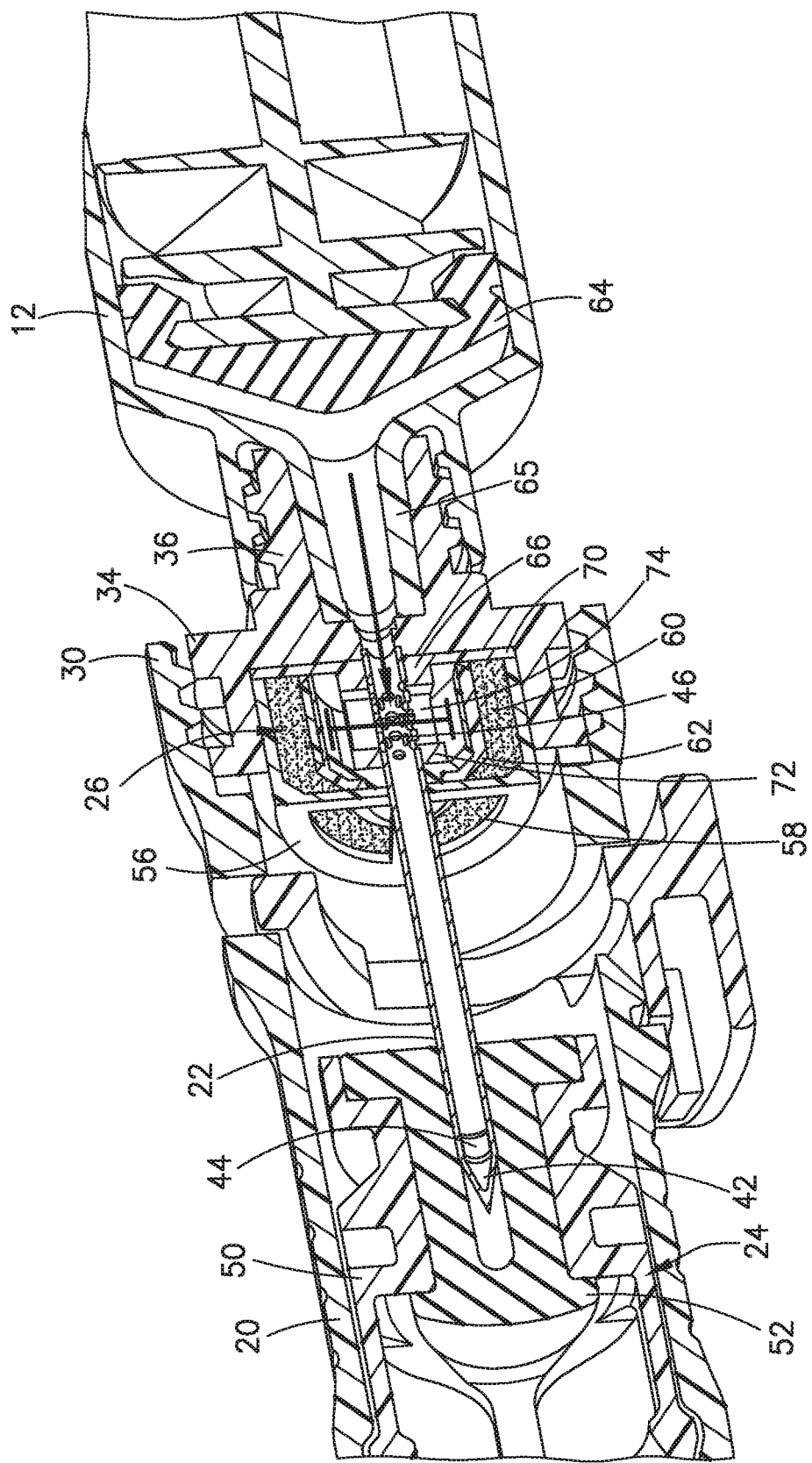
FIG. 7 is a partial cross-sectional view of the syringe adapter of FIG. 1, showing a closed path through a one-way valve.
Figure 8:
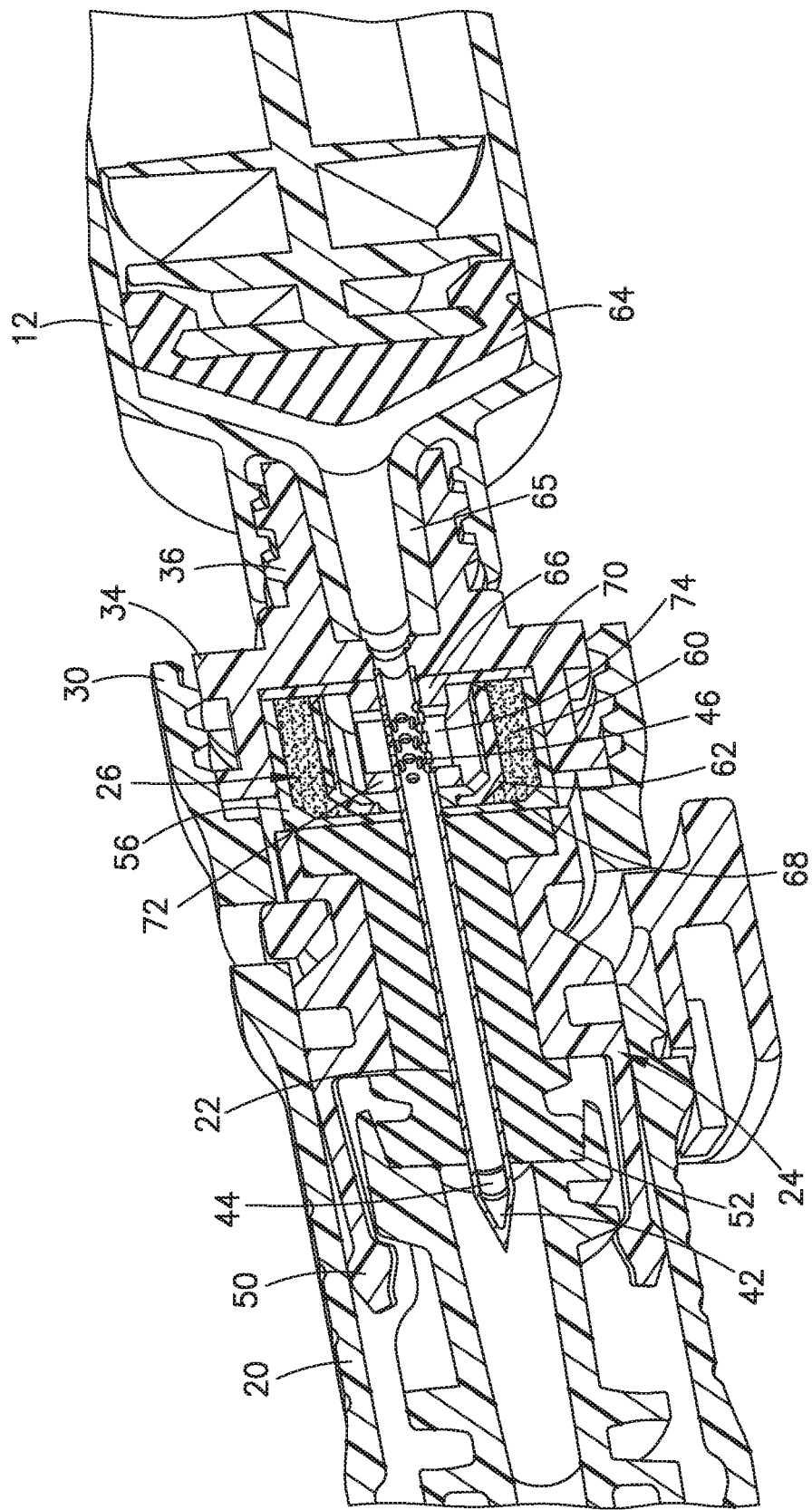
FIG. 8 is a partial cross-sectional view of the syringe adapter of FIG. 1, showing a second position of a seal arrangement and highlighting a seal interface between the seal arrangement and an aspiration assembly.
Figure 9:
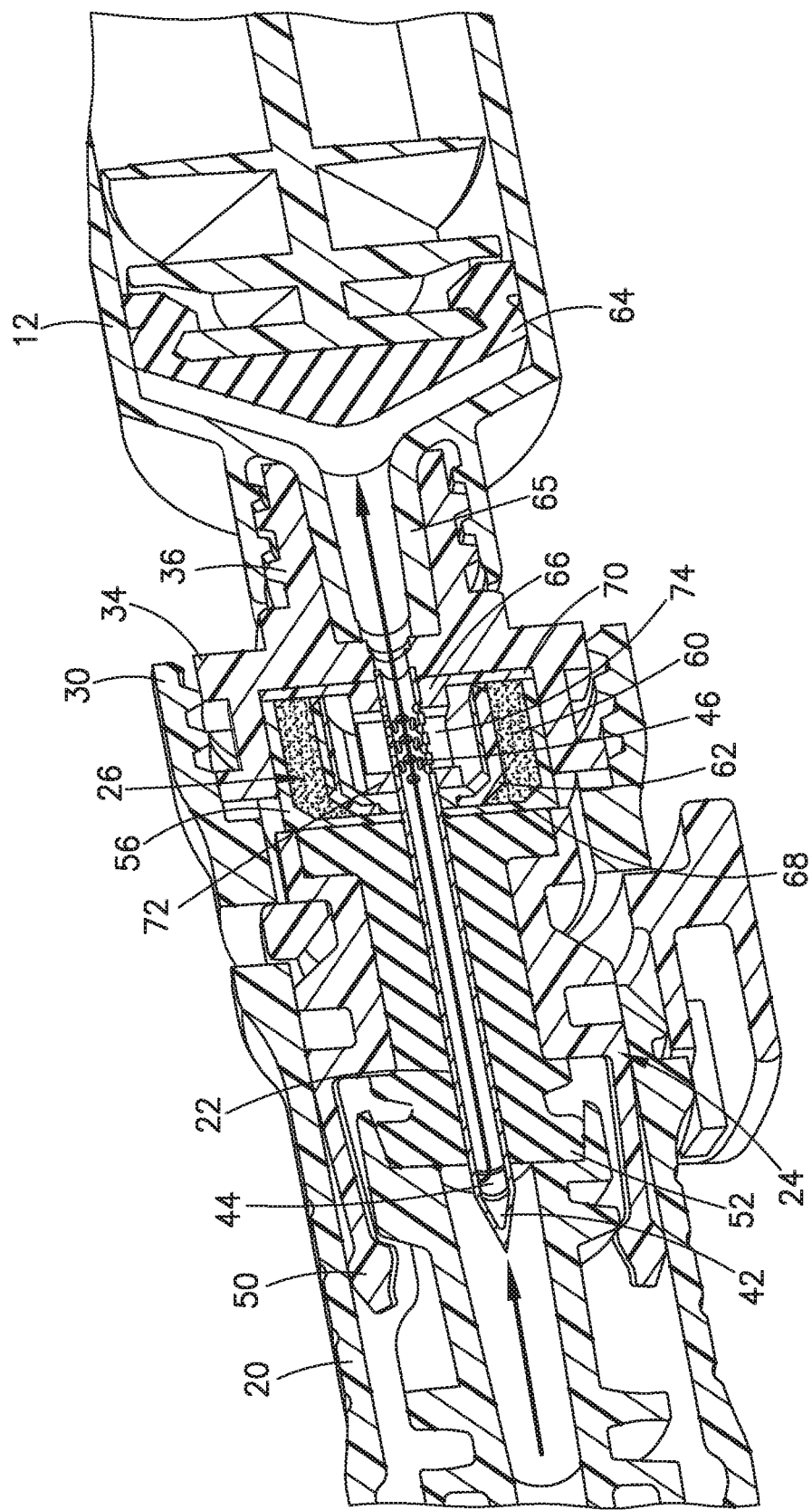
FIG. 9 is a partial cross-sectional view of the syringe adapter of FIG. 1, showing a second position of a seal arrangement and a flow path through the syringe adapter into a syringe.
Figure 10:
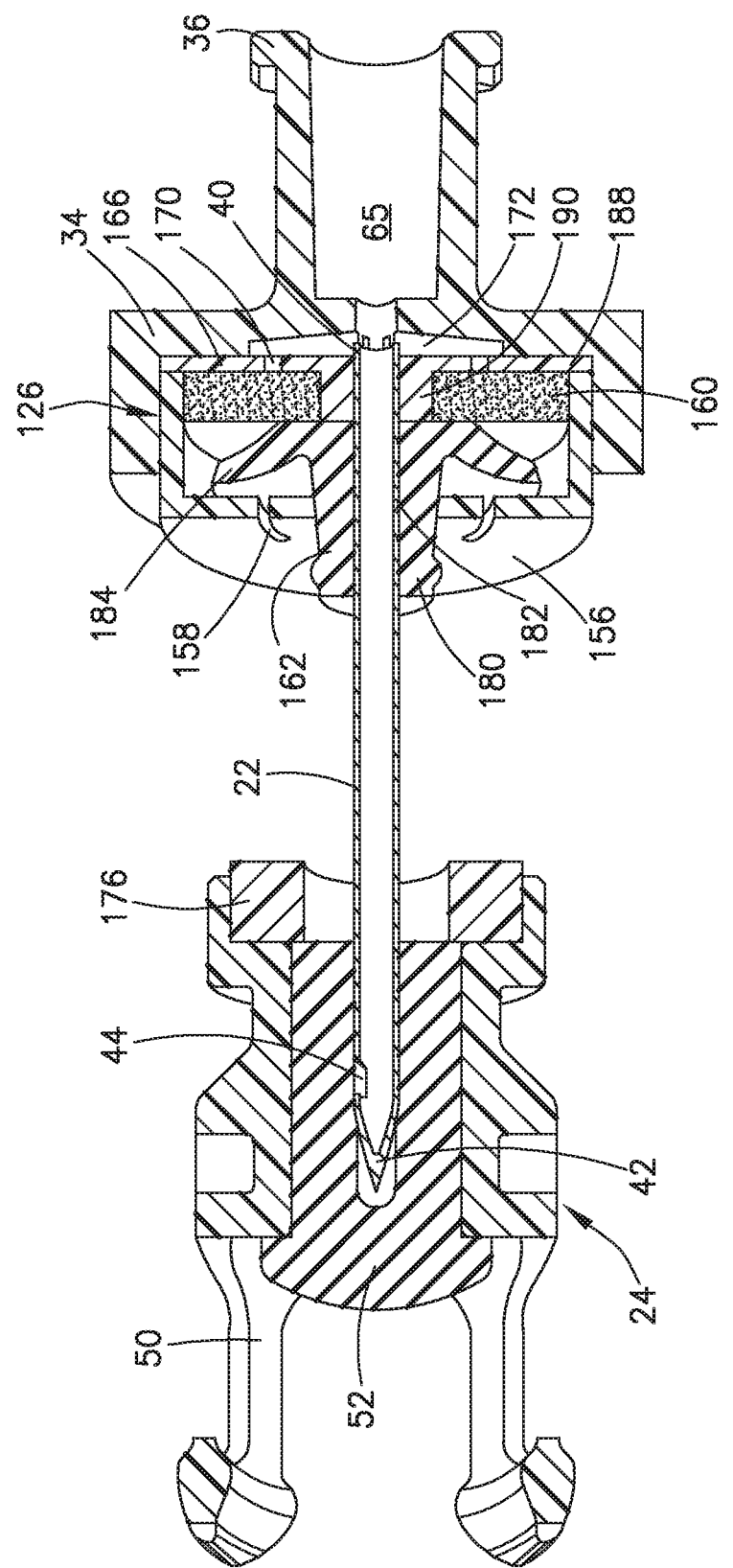
FIG. 10 is a cross-sectional view of an aspiration assembly according to a further aspect of the present invention.
Figure 11:
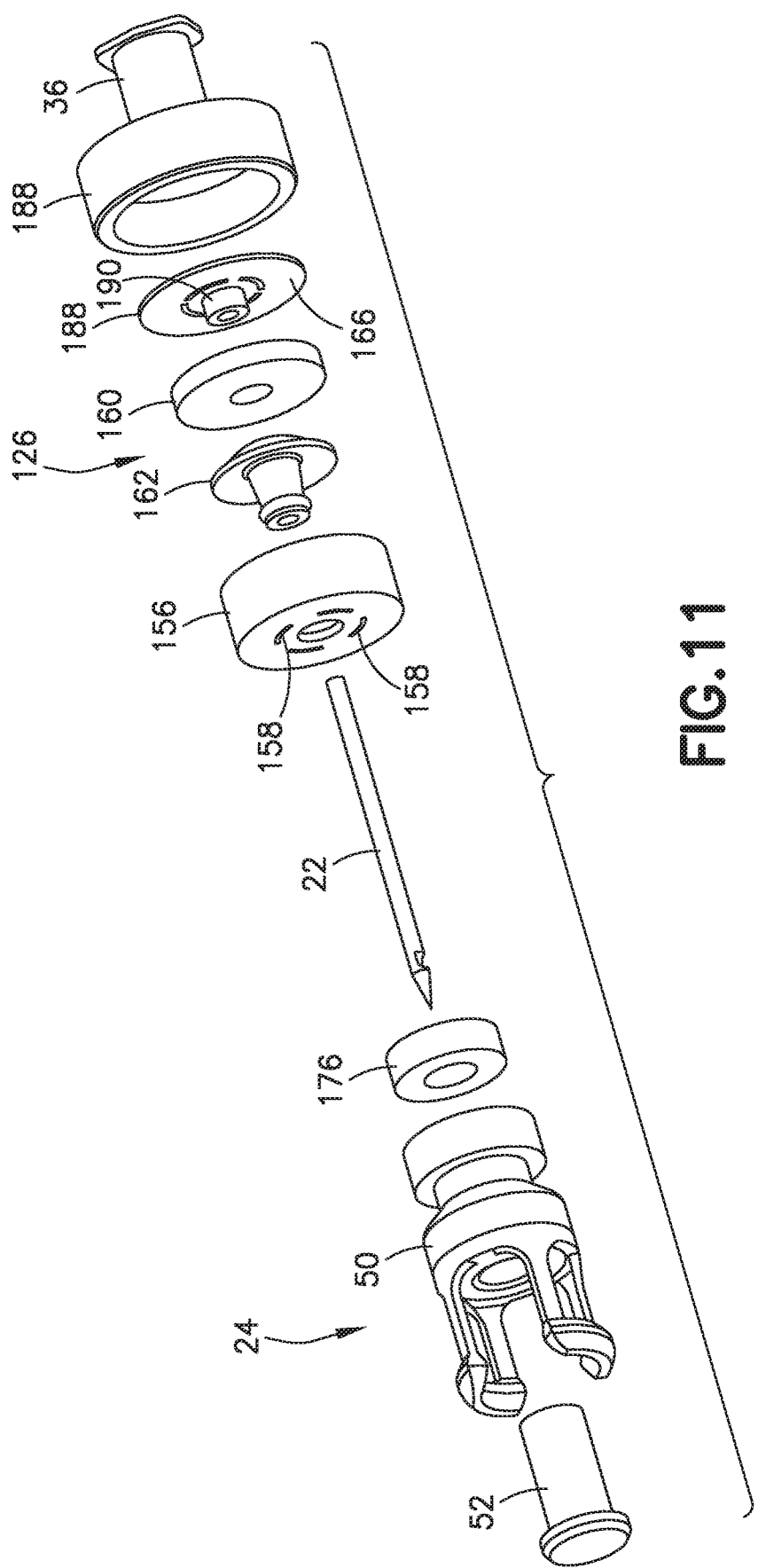
FIG. 11 is an exploded perspective view of the aspiration assembly of FIG. 10.

As shown in FIG. 7, the one-way valve 62 prevents the flow of fluid from the one-way valve 62 to the filter 60 and to the aspiration opening 58 of the aspiration housing 56. As shown in FIGS. 8 and 9, the membrane 52 of the seal arrangement 24 engages and seals the aspiration opening 58 of the aspiration housing 56 when the seal arrangement 24 is in the second position. In particular, the membrane 52 of the seal arrangement 24 forms a sealed interface 68 with the aspiration assembly 26, as highlighted in FIG. 8, to prevent the possibility of any fluid or contamination from entering or exiting the housing 20 via the aspiration assembly 26. A separate sealing gasket or surface may be secured to the sealing arrangement 24 rather than utilizing the membrane 52 to seal against the aspiration assembly 26.

Referring to FIGS. 6-9, at least a portion of the aspiration assembly 26 is received within the connector body 34. In one aspect, the filter 60 and one-way valve 62 are annular with the one-way valve 62 received within the filter 60. The aspiration housing 56 is cylindrical, although other suitable shapes and configurations may be utilized. The base 66 includes a planar, circular portion 70 with a cylindrical extension 72 extending from the planar, circular portion 70. The cylindrical extension 72 defines one or more openings 74 that are in fluid communication with the aspiration housing 56. The valve opening 46 of the cannula 22 is positioned within the base 66, with the opening 74 of the base 66 in fluid communication with the valve opening 46 of the cannula 22. The valve opening 46 of the cannula 22 may include one or more openings 46 as shown in FIGS. 6-9.

Referring to FIGS. 4-9, the one-way valve 62 includes a valve body 76 and a valve member 78 moveable radially inward relative to the valve body 76. The valve member 78 of the one-way valve 62 is elastomeric, although other suitable materials may be utilized. The valve member 78 may be over-molded onto the valve body 76, although other suitable arrangements may be utilized. The valve member 78 includes angled surfaces 80 that cooperate with corresponding angled surfaces 82 of the valve body 76 to only allow radially inward movement of the valve member 78. Accordingly, the one-way valve 62 only permits aspiration of air into the one-way valve 62 (FIG. 6) and into the aspiration assembly 26 with air moving from the syringe 12 into the aspiration assembly 26 (FIG. 7) causing the angled surfaces 80 of the valve member 78 to engage and seal against the angled surfaces 82 of the valve body 76 hereby preventing flow through the one-way valve 62. Due to the positioning of the one-way valve 62 within the filter 60, the filter 60 is also configured to prevent the valve member 78 from moving radially outward. In other words, the filter 60 restricts any radially outward movement of the valve member 78. During aspiration into the syringe 12, the filter 60 is configured to filter any contamination from the air as the air is aspirated into the syringe 12 through the aspiration assembly 26. The filter 60 may be hydrophobic and/or oleophobic.

Figure 12:
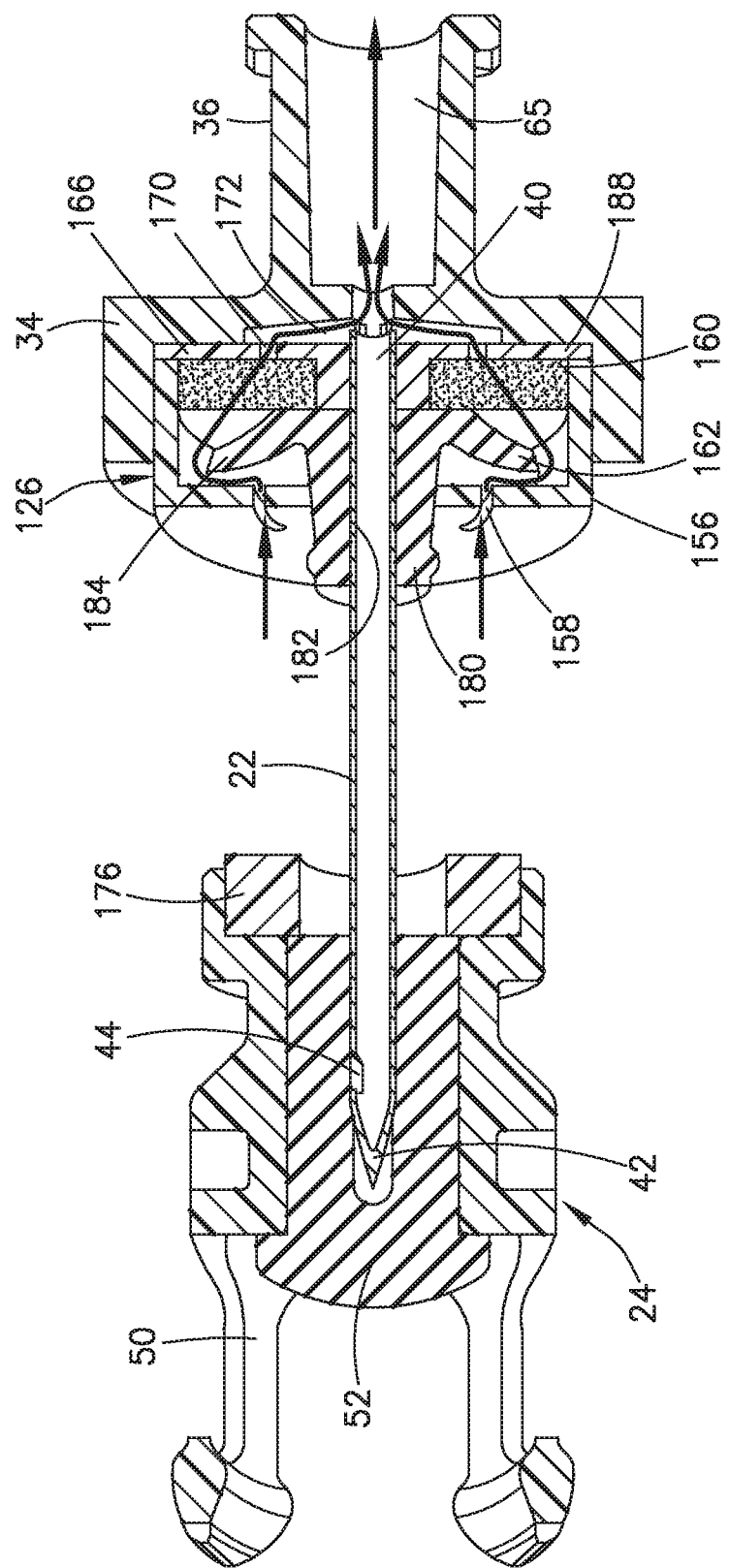
FIG. 12 is a cross-sectional view of the aspiration assembly of FIG. 10, showing a flow path through the aspiration assembly.

Referring to FIGS. 10-18, an aspiration assembly 126 according to a further aspect of the present invention is provided. The aspiration assembly 126 is similar to the aspiration assembly 26 of FIGS. 1-9 and functions in a similar manner. The aspiration assembly 126 is incorporated within a syringe adapter in a similar manner as the aspiration assembly 26 of FIGS. 1-9. The aspiration assembly 126 of FIGS. 10-18 includes an aspiration housing 156 defining an aspiration opening 158, a filter 160 received by the aspiration housing 156, and a one-way valve 162 received by the aspiration housing 156, where air is configured to flow into the aspiration housing 156 via the aspiration opening 158, through the one-way valve 162, and through the filter 160. The aspiration assembly 126 includes a base 166 secured to the aspiration housing 156 and engaging the filter 160. Rather than providing the valve opening 46 in the cannula 22 as in the syringe adapter 10 of FIGS. 1-9, the base 166 defines an opening 170 and the connector body 34 defines an opening 172. The opening 172 of the connector body 34 is in fluid communication with the opening 170 of the base 166 and the central passageway 65 of the connector body 34. Accordingly, as shown in FIG. 12, a flow path is provided through the aspiration opening 158 of the aspiration housing 156, past the one-way valve 162, through the filter 160, through the opening 170 in the base 166, through the opening 172 of the connector body 34, and into the central passageway 65 of the connector body 34.

Figure 13:
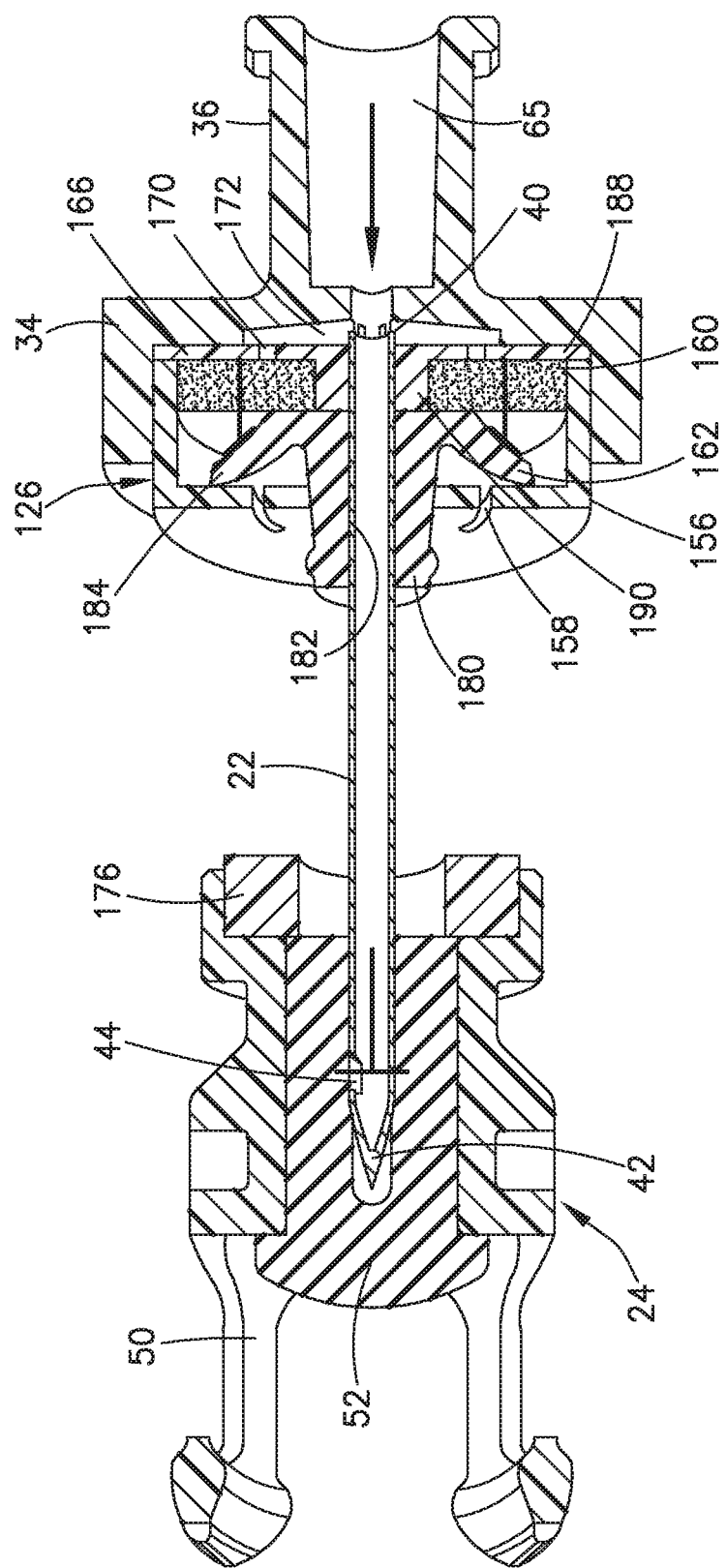
FIG. 13 is a cross-sectional view of the aspiration assembly of FIG. 10, showing a closed path through a one-way valve.
Figure 14:
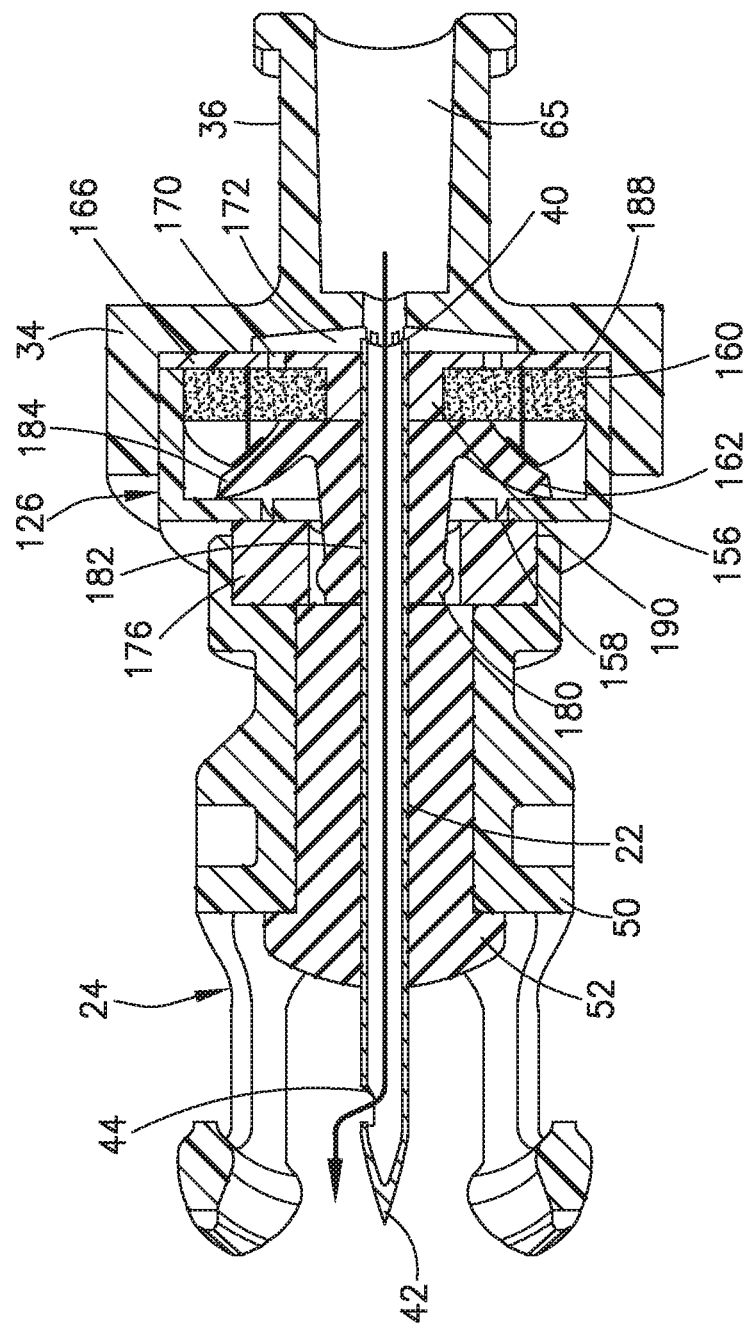
FIG. 14 is a cross-sectional view of the aspiration assembly of FIG. 10, showing a seal arrangement in a second position.
Figure 15:
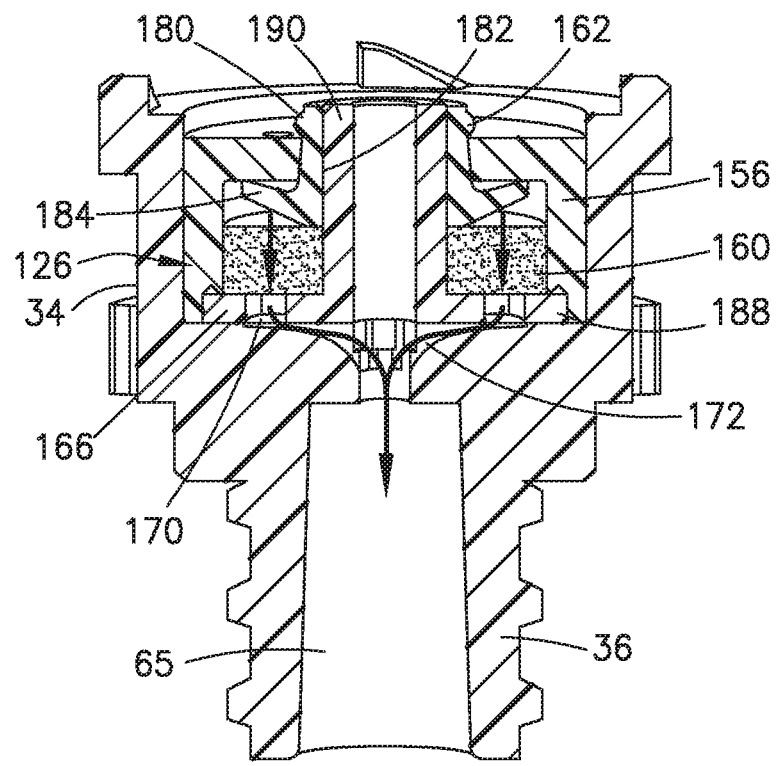
FIG. 15 is a cross-sectional view of the aspiration assembly of FIG. 10, showing a flow path through the aspiration assembly and into a connector body.
Figure 16:
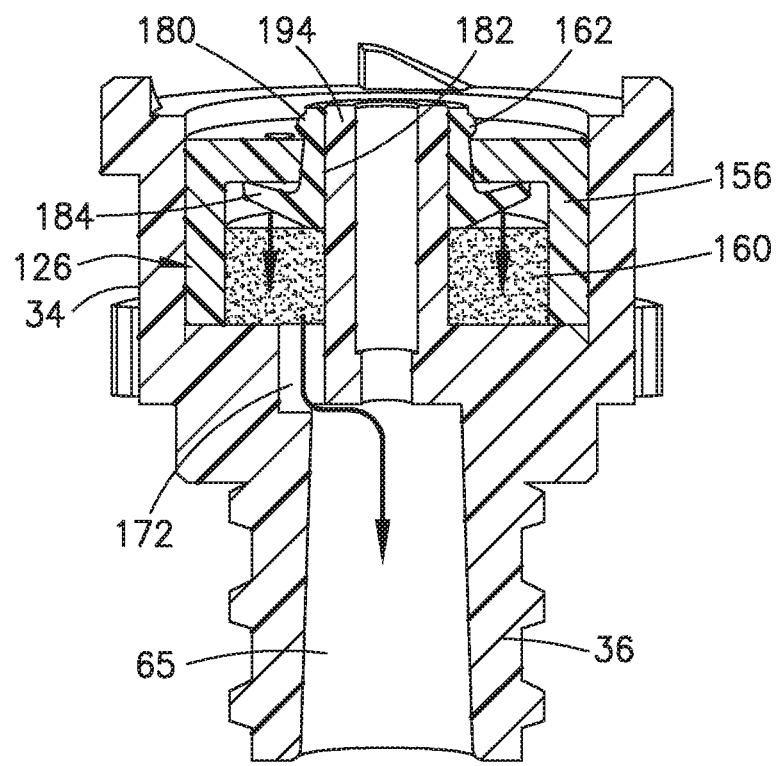
FIG. 16 is a cross-sectional view of the aspiration assembly of FIG. 10, showing a flow path arrangement and configuration pursuant to a further aspect of the present invention.
Figure 17:
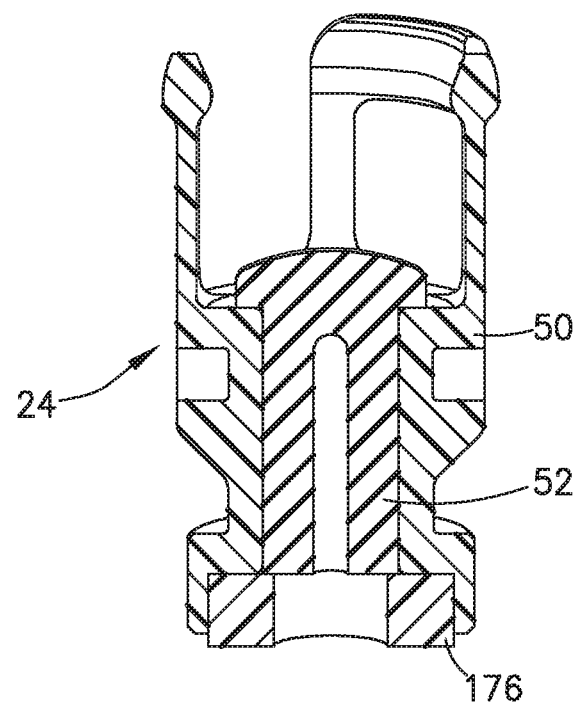
FIG. 17 is a cross-sectional view of a seal arrangement according to one aspect of the present invention.
Figure 18:
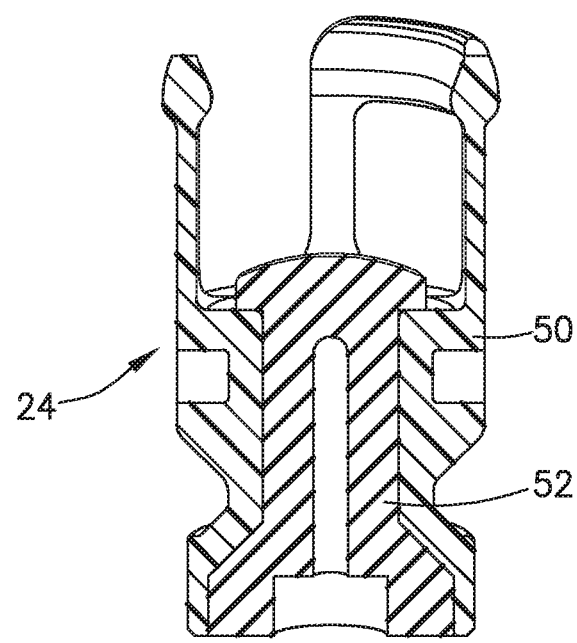
FIG. 18 is a cross-sectional view of a seal arrangement according to a further aspect of the present invention.

Referring to FIGS. 12-18, the first end 40 of the cannula 22 is secured to the connector body 34, with the cannula 22 extending through the filter 160, the one-way valve 162, and the aspiration housing 158 with the second end 42 of the cannula 22 configured to be received by the seal arrangement 24. The one-way valve 162 prevents the flow of fluid from within the aspiration housing 156 to the aspiration opening 158. As with the syringe adapter 10 discussed above in connection with FIGS. 1-9, the seal arrangement 24 engages and seals the aspiration opening 158 of the aspiration housing 156 when the seal arrangement 24 is in the second position. The membrane 52 of the seal arrangement 24 may engage and seal the aspiration opening 158 as shown in FIGS. 14 and 17. Alternatively, in a further aspect shown in FIG. 18, a sealing gasket 176 is received by the collet 50 with the sealing gasket 176 engaging and sealing the aspiration opening 158 of the aspiration housing 156. The one-way valve 162 is an umbrella valve, although other suitable arrangements may be provided. The one-way valve 162 includes a central body 180 defining a passageway 182 and an umbrella-shaped flange 184 extending from the central body 180. As shown in FIG. 12, the umbrella-shaped flange 184 is resilient and configured to lift away from the aspiration opening 158 of the aspiration housing 156 when air is aspirated via the syringe 12 through the aspiration opening 158 towards the opening 170 in the base 166 and the opening 172 in the connector body 34. In particular, withdrawing the plunger 64 of the syringe 12 will cause a pressure drop within the aspiration housing 156, which opens the one-way valve 162 and draws in air via the aspiration opening 158 as discussed above. As shown in FIGS. 13 and 14, air or fluid flowing through the central passageway 65 of the connector body 34, into the opening 172 of the connector body 34, into the opening 170 of the base 166, and into the aspiration housing 156 will force the umbrella-shaped flange 184 of the one-way valve 162 against the aspiration housing 156 to block the aspiration opening 158. Although a plurality of aspiration openings 158 are shown, one or more aspiration openings 158 may be provided. During aspiration, the filter 160 will filter any contamination passing through the aspiration housing 156 to the connector body 34. The filter 160 may be hydrophobic and/or oleophobic.

The aspiration housing 156 is cylindrical, although other suitable shapes and configurations may be utilized. The base 166 includes a planar, circular portion 188 with a cylindrical extension 190 extending from the planar, circular portion 188. The filter 160 is annular and positioned over the cylindrical extension 190 of the base 166. The cylindrical extension 190 of the base 166 also extends through the passageway 182 of the central body 180 of the one-way valve 162. A portion of the one-way valve 162 and the base 166 extend from the aspiration housing 156, although other suitable arrangements may be utilized.

Referring to FIG. 16, rather than providing the base 166 as shown in FIG. 15, the connector body 34 may be provided with a cylindrical extension 194 that extends through the filter 160, the one-way valve 162, and the aspiration housing 156. The opening 172 of the connector body 34 is directly in fluid communication with the aspiration housing 156 with a fluid path formed through the aspiration opening 158, past the one-way valve 162, into the aspiration housing 156, through the filter 160, into the opening 172 of the connector body 34, which leads to the central passageway 65 of the connector body 34.

Although the invention has been described in detail for the purpose of illustration based on what is currently considered to be the most practical and preferred aspects, it is to be understood that such detail is solely for that purpose and that the invention is not limited to the disclosed aspects, but, on the contrary, is intended to cover modifications and equivalent arrangements that are within the spirit and scope of the appended claims. For example, it is to be understood that the present invention contemplates that, to the extent possible, one or more features of any aspect can be combined with one or more features of any other aspect.

The invention claimed is:

1. A syringe adapter comprising:
   a housing having a first end and a second end positioned opposite the first end, the housing including a connector body positioned at the first end of the housing and configured to be secured to a syringe barrel;
   a cannula positioned within the housing, the cannula having a first end and a second end opposite the first end, the cannula defining a transfer opening and a valve opening;
   a seal arrangement positioned within the housing and movable within the housing, the seal arrangement comprising a membrane; and
   an aspiration assembly positioned within the housing comprising:
      an aspiration housing defining an aspiration opening;
      a filter received by the aspiration housing; and
      a one-way valve received by the aspiration housing, wherein the valve opening of the cannula is positioned within the aspiration housing, and wherein air is configured to flow into the filter via the aspiration opening, into the one-way valve, and into the valve opening of the cannula.

2. The syringe adapter of claim 1, wherein the aspiration assembly further comprises a base secured to the aspiration housing and engaging the filter and the one-way valve.

3. The syringe adapter of claim 2, wherein the base is secured to the connector body.

4. The syringe adapter of claim 2, wherein the first end of the cannula is secured to the connector body, the cannula extending through the base, the one-way valve, the filter, and the aspiration housing with the second end of the cannula configured to be received by the seal arrangement.

5. The syringe adapter of claim 1, wherein the one-way valve prevents the flow of fluid from the one-way valve to the filter and to the aspiration opening of the aspiration housing.

6. The syringe adapter of claim 1, wherein the seal arrangement has a first position with the second end of the cannula received within the membrane of the seal arrangement and a second position with the second end of the cannula positioned outside of the membrane of the seal arrangement, the membrane of the seal arrangement engaging and sealing the aspiration opening of the aspiration housing when the seal arrangement is in the second position.

7. The syringe adapter of claim 1, wherein at least a portion of the aspiration assembly is received within the connector body.

8. The syringe adapter of claim 1, wherein the valve opening of the cannula comprises a plurality of openings.

9. The syringe adapter of claim 1, wherein the filter and the one-way valve are annular, and wherein the one-way valve is received within the filter.

10. The syringe adapter of claim 1, wherein the one-way valve comprises a valve body and a valve member moveable radially inward relative to the valve body.

11. The syringe adapter of claim 1, wherein the valve member of the one-way valve is elastomeric.

12. A syringe adapter comprising:
a housing having a first end and a second end positioned opposite the first end, the housing including a connector body positioned at the first end of the housing and configured to be secured to a syringe barrel;
a cannula positioned within the housing, the cannula having a first end and a second end opposite the first end;
a seal arrangement positioned within the housing and movable within the housing, the seal arrangement comprising a membrane; and
an aspiration assembly positioned within the housing comprising:
an aspiration housing defining an aspiration opening;
a filter received by the aspiration housing; and
a one-way valve received by the aspiration housing, wherein air is configured to flow into the aspiration housing via the aspiration opening, through the one-way valve, and through the filter.

13. The syringe adapter of claim 12, wherein the aspiration assembly further comprises a base secured to the aspiration housing and engaging the filter.

14. The syringe adapter of claim 13, wherein the base defines an opening and the connector body defines an opening in fluid communication with the opening of the base and a central passageway of the connector body.

15. The syringe adapter of claim 12, wherein the connector body defines an opening in fluid communication with the aspiration housing and a central passageway of the connector body, and wherein air is configured to pass through the filter and enter the opening of the connector body.

16. The syringe adapter of claim 12, wherein the first end of the cannula is secured to the connector body, the cannula extending through the filter, the one-way valve, and the aspiration housing with the second end of the cannula configured to be received by the seal arrangement.

17. The syringe adapter of claim 12, wherein the one-way valve prevents the flow of fluid from within the aspiration housing to the aspiration opening.

18. The syringe adapter of claim 12, wherein the seal arrangement has a first position with the second end of the cannula received within the membrane of the seal arrangement and a second position with the second end of the cannula positioned outside of the membrane of the seal arrangement, the seal arrangement engaging and sealing the aspiration opening of the aspiration housing when the seal arrangement is in the second position.

19. The syringe adapter of claim 18, wherein one of the membrane and a sealing gasket seals the aspiration opening of the aspiration housing when the seal arrangement is in the second position.

20. The syringe adapter of claim 12, wherein the one-way valve comprises an umbrella valve.

* * * * *